United States Patent [19]
Bondinell et al.

[11] 4,128,666
[45] Dec. 5, 1978

[54] 4 AND 5-HALO SUBSTITUTED 2-INDANAMINE COMPOUNDS

[75] Inventors: William E. Bondinell, Cherry Hill, N.J.; Robert G. Pendleton, Philadelphia, Pa.

[73] Assignee: SmithKline Corporation, Philadelphia, Pa.

[21] Appl. No.: 825,623

[22] Filed: Aug. 18, 1977

[51] Int. Cl.² .............................................. A01N 9/20
[52] U.S. Cl. ..................................... 424/330; 260/578
[58] Field of Search ........................ 260/578; 424/330

[56] References Cited

U.S. PATENT DOCUMENTS

| | | |
|---|---|---|
| 2,982,783 | 5/1961 | Schenck et al. ............... 260/578 X |
| 3,060,091 | 10/1962 | Witkin ............................ 260/578 X |
| 3,178,478 | 4/1965 | Huebner .......................... 260/578 |

*Primary Examiner*—Paul F. Shaver
*Attorney, Agent, or Firm*—Joseph A. Marlino; Richard D. Foggio; William H. Edgerton

[57] ABSTRACT

2-Indanamine compounds having 4 and 5-halo substituents are inhibitors of phenylethanolamine N-methyltransferase.

6 Claims, No Drawings

4 AND 5-HALO SUBSTITUTED 2-INDANAMINE COMPOUNDS

This invention relates to a new 2-indanamine compounds having 4 and 5-halo substituents. These compounds have pharmacological activity, in particular they inhibit the enzyme phenylethanolamine N-methyltransferase.

Epinephrine is a hormone, synthesized in the adrenal medulla, which is released into the blood stream in response to stress and produces profound physiological changes which serve to prepare the animal to cope with the stressor situation. For example, epinephrine produces anxiety, an increase in blood pressure, acceleration of heart rate and increase in cardiac output. These changes are detrimental in individuals with certain disease conditions such as angina pectoris, myocardial infarction and anxiety neuroses.

Phenylethanolamine N-methyltransferase catalyzes the final step in the biosynthesis of epinephrine, that is the transfer of a methyl group from S-adenosylmethionine to norepinephrine to produce epinephrine.

The compounds of this invention inhibit phenylethanolamine N-methyltransferase and thus reduce the formation of epinephrine. They are therefore useful in situations where there is overproduction of epinephrine or where epinephrine production is detrimental.

The compounds of this invention are represented by the following formula:

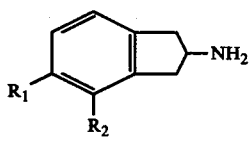

FORMULA 1 in which:

$R_1$ and $R_2$ are chloro, bromo, fluoro, trifluoromethyl or iodo, $R_1$ and $R_2$ being the same or different and pharmaceutically acceptable acid addition salts thereof.

The compounds of this invention are prepared by the following procedure:

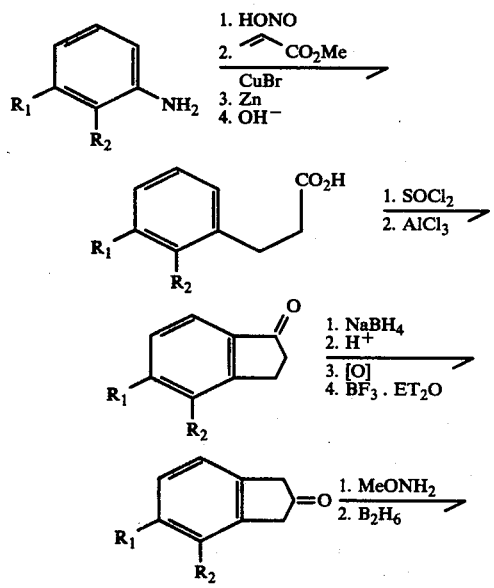

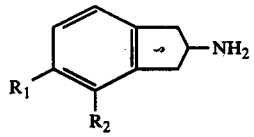

The terms $R_1$ and $R_2$ are as defined above.

According to the above procedure, the 2-imdanamines are prepared by reacting a 2,3 substituted aniline with nitrous acid, methyl acrylate and cuprous bromide to form the corresponding disubstituted phenylpropionic acid. The acid is cyclized to the 1-indanone which in turn is converted to the 2-indanone and reduced to the desired 2-indanamine. The cyclization is carried out by treating the phenylpropionic acid with thionyl chloride and aluminum chloride.

An alternative method of preparing the phenylpropionic acid may be carried out by brominating a 2,3 substituted toluene and alkylating the resultant compound with diethyl malonate. The cyclization of the phenylpropionic acid may also be carried out with an acid catalyst such as polyphosphoric acid.

Pharmaceutically acceptable, acid addition salts of the compounds of Formula 1 are formed with organic and inorganic acids by methods known to the art. The base is reacted with an organic or inorganic acid in aqueous miscible solvent, such as acetone or ethanol, with isolation of the salt by concentration and cooling or in aqueous immiscible solvent, such as ethyl ether or chloroform, with the desired salt separating directly. Exemplary of the salts which are included in this invention are maleate, fumarate, benzoate, ascorbate, pamoate, succinate, bismethylenesalicylate, methanesulfonate, ethanedisulfonate, benzenesulfonate, acetate, propionate, tartrate, salicylate, citrate, gluconate, lactate, malate, mandelate, cinnamate, citraconate, aspartate, stearate, palmitate, itaconate, glycolate, p-aminobenzoate, glutamate, theophylline acetates, hydrochloride, hydrobromide, sulfate, cyclohexylsulfamate, phosphate and nitrate salts.

2-Indanamines and 2-aminodihalo substituted indanes are generally known in the art. The latter compounds are disclosed in German Patent No. 1,518,652 as analgetics and vasodilators.

The basic activity of the compounds of this invention is demonstrated by inhibition of phenylethanolamine N-methyltransferase in vitro by the assay procedure described by Pendleton and Snow, Molecular Pharmacology, 9:718–725, 1973 and Pendleton et al., Res. Comm. Chem. Path. Pharm. 17:201–213, 1977, at various compound concentrations. From the data received, the enzyme inhibition dissociation constants ($K_i$ values) were calculated according to mathematical procedures described by Chou, Mol. Pharm. 10:235–247, 1974. The $K_i$ value is an inverse function of the affinity of the inhibitor for the enzyme so that the lower the number, the more potent the compound.

The $K_i$ value of a preferred compound of this invention, 4,5-dichloro-2-indanamine, was compared with other closely related compounds. Following are the results:

TABLE I

| SK&F Number | Structure | $K_i$ |
|---|---|---|
| 82520 | 4,5-dichloro-1-aminoindane (NH₂ at 1-position, Cl at 4,5) | $4 \times 10^{-7}$ M |
| 82566 | 4,5-dichloro-2-aminoindane | $2 \times 10^{-8}$ M |
| 82570 | 4,5-dichloro-1-aminoindane (isomer) | $>1 \times 10^{-6}$ M |
| 50070 | 5,6-dichloro-2-aminoindane | $1 \times 10^{-6}$ M |
| 8851 | 2-aminoindane | $1 \times 10^{-5}$ M |

The results clearly demonstrate that both the position of the amino group and the dichloro substituents determine the potency of inhibition. The 2-amino-4,5 dichloroindane (82566) is a much more potent inhibitor than the other compounds.

In addition, the activity of the compounds of this invention is demonstrated in vivo by administration to mice at 50 mg./kg. for seven consecutive days. Male mice were dosed orally with either drug or vehicle control on a twice-a-day basis for seven consecutive days.

On the morning of the next day they were again dosed with two hours later sacrificed by decapitation. The adrenal glands were then removed and analyzed fluorometrically for both epinephrine and norepinephrine content. A compound is considered active as a PNMT inhibitor if it significantly (at least $p<.05$) decreases the adrenal epinephrine/norepinephrine ratio, as we have previously shown to be the case with other PNMT inhibitors (R.G. Pendleton et al., J. Pharmacol. Exp. Ther. 190:551–562, 1974 and R.G. Pendleton et al., J. Pharmacol. Exp. Ther. 197:623–632, 1976).

TABLE II

| Experiment | Compound | Daily Dose (mg/kg, p.o.) | $n^a$ | E NE Ratio |
|---|---|---|---|---|
| 1 | Control | | 5 | 2.6 ± .1 |
|   | SK & F 8851 | 50 | 5 | 2.4 ± .04 |
|   | SK & F 82566 | 50 | 5 | 1.1 ± $.2^b$ |
|   | SK & F 50070 | 50 | 5 | 2.2 ± .3 |
| 2 | Control | | 5 | 2.0 ± .05 |
|   | SK & F 82520 | 50 | 5 | 1.8 ± 0.2 |

$^a$Number of mice/group
$^b$Significantly different from control group (p <.001)

The in vivo results indicate once again that the position of the amino and dichloro moieties is critical in that only Sk&F 82566 significantly lowered the adrenal epinephrine/norepinephrine ratio under the conditions of this study.

The pharmaceutical compositions of this invention to inhibit phenylethanolamine N-methyltransferase comprise a pharmaceutical carrier and, as the active ingredient, a 2-indanamine compound of Formula I. The active ingredient will be present in the compositions of this invention in an effective amount to inhibit phenylethanolamine N-methyltransferase.

Preferably, the compositions of this invention contain the active ingredient of Formula I in an amount of from about 50 mg. to about 1000 mg., advantageously from about 100 mg. to about 500 mg., per dosage unit.

The pharmaceutical carrier may be for example a solid or a liquid. Exemplary of solid carriers are lactose, magnesium stearate, terra alba, sucrose, talc, stearic acid, gelatin, agar, pectin or acacia. The amount of solid carrier will vary widely but preferably will be from about 25 mg. to about 1 gm. Exemplary of liquid carriers are syrup, peanut oil, olive oil, sesame oil, propylene glycol, polyethylene glycol (mol. wt. 200–400) and water. The carrier or diluent may include a time delay material well known to the art such as, for example, glyceryl monostearate or glyceryl distearate alone or with a wax.

A wide variety of pharmaceutical forms can be employed, for example, the preparation may take the form of tablets, capsules, powders, troches, lozenges, syrups, emulsions, sterile injectable liquids or liquid suspensions or solutions.

The pharmaceutical compositions are prepared by conventional techniques involving procedures such as mixing, granulating and compressing or dissolving the ingredients as appropriate to the desired preparation.

The method of inhibiting phenylethanolamine N-methyltransferase, according to this invention, comprises administering to an animal in an amount sufficient to inhibit phenylethanolamine N-methyltransferase a 2-indanamine compound of Formula I.

Preferably, the compounds of Formula I are administered in conventional dosage unit forms prepared by combining an appropriate dose of the compound with standard pharmaceutical carriers.

Preferably, the active ingredient of Formula I will be administered in a daily dosage regimen of from about 100 mg. to about 2000 mg., most preferably from about 200 mg. to about 1000 mg. Advantageously, equal doses will be administered preferably two to three times per day. When the administration is carried out as described above, inhibition of phenylethanolamine N-methyltransferase is produced.

The route of administration of the pharmaceutical compositions of this invention and in accordance with the methods of this invention is internal, either parenteral or preferably oral, in an amount to produce the desired biological activity.

The following examples are not limiting but are illustrative of this invention.

EXAMPLE 1

8.1 g of 2,3-Dichloroaniline (0.05 mole) in acetone (100 ml.) and concentrated hydrobromic acid (16 ml.) was stirred at −5° C. and treated with a solution of 4.2 g. of sodium nitrite (0.06 mole) in water (10 ml.). Methyl acrylate (0.5 mole) (43 g.) and cuprous bromide (100 mg.) were then added at 0° C. The reaction temperature was kept below 15° C. until nitrogen evolution ceased and then stirred at 25° C. for thirty minutes. The reaction mixture was poured into water and extracted with benzene which was dried over sodium sulfate and evaporated to give methyl 2-bromo-3-(2,3-dichlorophenyl)-propionate. The propionate, 156 g. (0.5 mole) was dissolved in glacial acetic acid (1 l.) and stirred. Zinc dust 65 g. (1 mole) was added in portions and the mixture was stirred for one hour, filtered and evaporated to give methyl 3-(2,3-dichlorophenyl)propionate.

Methyl 3-(2,3-dichlorophenyl)propionate was refluxed in 10% aqueous sodium hydroxide (1 l.) for two hours and the reaction mixture was cooled, acidified and filtered. The filter cake was dissolved in hot aqueous sodium bicarbonate, and filtered. The filtrate was acidified and filtered to yield 3-(2,3-dichlorophenyl)-propionic acid.

The propionic acid 2.7 g. (0.011 mole) was suspended in benzene (27 ml.) and treated with 1.7 g. of thionyl chloride (0.014 mole) and dimethyl formamide (two drops). The reaction was refluxed for thirty minutes, filtered and evaporated to give 3-(2,3-dichlorophenyl)-propionyl chloride which was dissolved in chlorobenzene (12 ml.) and treated with anhydrous aluminum chloride 2.4 g. (18 mmoles). The reaction was stirred for one hour and poured onto ice. The chlorobenzene was evaporated in vacuo and the residue was extracted with chloroform which was washed, dried over sodium sulfate and evaporated to give 4,5-dichloro-1-indanone.

The above prepared indanone 2.0 g. (0.01 mole) was dissolved in ethanol (30 ml.) and treated with 0.5 g. of sodium borohydride (0.013 mole). The reaction was stirred at 25° C. for one hour and evaporated. Ether was added to the residue followed by 10% hydrochloric acid. The ether was dried and evaporated to yield 4,5-dichloro1-indanol.

2.0 g. of the indanol (0.01 mole) and a trace of p-toluenesulfonic acid in benzene (30 ml.) was refluxed for four hours. The benzene solution was evaporated to give 4,5-dichloro-1-indene and 4,5-dichloro-2-indene.

9.3 g. of the above mixture of indenes (0.05 mole) in chloroform (125 ml.) was treated with 10.0 g. of m-chloroperbenzoic acid (0.05 mole) at 5° C. The solution was allowed to warm to 25° C. and was stirred for 16 hours. The chloroform was evaporated and the residue was dissolved in carbon tetrachloride which was extracted with aqueous sodium bicarbonate, dried and evaporated to give a mixture of 4,5-dichloro-1,2-epoxyindane and 4,5-dichloro-2,3-epoxyindane.

The mixture of above epoxyindanes was dissolved in ether (100 ml.) and cooled. Boron trifluoride etherate (100 ml.) was added below 15° C. and the reaction was stirred for thirty minutes. Water was added slowly and the ether layer was separated, washed with aqueous sodium bicarbonate, dried over sodium sulfate and evaporated. The residue was chromatographed on silica gel eluted with benzene to give 4,5-dichloro-2-indanone.

4,5-Dichloro-2-indanone 4.2 g. (0.02 mole) and 4.2 g. of methoxyamine hydrochloride (0.05 mole) were dissolved in a mixture of ethanol (42 ml.) and pyridine (42 ml.) and heated on a steam bath for thirty minutes. The reaction was diluted with water and the O-methyl oxime of 4,5-dichloro-2-indanone was isolated by filtration.

1.0 g. of the O-methyl oxime of 4,5-dichloro-2-indanone (4mmoles) dissolved in tetrahydrofuran (5 ml.) was treated with 1 M diborane in tetrahydrofuran (20 ml.) and refluxed for two hours in an argon atmosphere. Methanol was added and the solvent was evaporated. The residue was treated with 10% hydrochloric acid and heated on a steam bath for thirty minutes. The mixture was made alkaline and extracted with ether which was dried over potassium carbonate and evaporated to yield 4,5-dichloro-2-indanamine. The bitartrate salt was recrystallized from methanol-ether, m.p. 215° C.

EXAMPLE 2

Following the procedure of Example 1, the following halo and trifluoromethyl substituted aniline compounds:
  3-bromo-2-chloraniline
  3-bromo-2-fluoroaniline
  2-chloro-3-fluoroaniline
  2,3-dibromoaniline
  2,3-difluoroaniline
  2,3-bis(trifluoromethyl)aniline
are used as starting materials to give the following products respectively:
  5-bromo-4-chloro-2-indanamine
  5-bromo-4-fluoro-2-indanamine
  4-chloro-5-fluoro-2-indanamine
  4,5-dibromo-2-indanamine
  4,5-difluoro-2-indanamine
  4,5-bis(trifluoromethyl)-2-indanamine

EXAMPLE 3

19.6 g. of 2-chloro-3-fluoronitrobenzene (0.11 mole) is reduced with stannous chloride (118 g., 0.63 mole) in 180 ml. of concentrated hydrochloric acid. The solution is basified with aqueous sodium hydroxide and extracted with chloroform to yield 2-chloro-3-fluoroaniline.

Substituting 2-chloro-3-fluoroaniline as a starting material for 2,3-dichloroaniline and following the procedure of Example 1 yields 4-chloro-5-fluoro-2-indanamine.

EXAMPLE 4

Following the procedure of Example 3 the following halo substituted nitrobenzene compounds:
  2-bromo-3-chloro-1-nitrobenzene
  2-bromo-3-iodo-1-nitrobenzene
  3-bromo-2-iodo-1-nitrobenzene
  3-chloro-2-fluoro-1-nitrobenzene
  3-chloro-2-iodo-1-nitrobenzene
  2,3-diiodo-1-nitrobenzene
are converted to the corresponding halo substituted anilines which are used as starting materials in the procedure of Example 1 to give the following products respectively:
  4-bromo-5-chloro-2-indanamine
  4-bromo-5-iodo-2-indanamine
  5-bromo-4-iodo-2-indanamine
  5-chloro-4-fluoro-2-indanamine
  5-chloro-4-iodo-2-indanamine
  4,5-diiodo-2-indanamine

EXAMPLE 5

| Ingredients | Mg./Capsule |
| --- | --- |
| 4,5-Dichloro-2-indanamine | 150 mg. |
| Lactose | 150 mg. |

The above ingredients are mixed and filled into a hard gelatin capsule.

One capsule is given three times a day.

EXAMPLE 6

| Ingredients | Mg./Tablet |
| --- | --- |
| 4,5-Dichloro-2-indanamine | 50 |
| Calcium sulfate dihydrate | 150 |
| Sucrose | 25 |
| Starch | 15 |
| Talc | 5 |
| Stearic Acid | 3 |

The sucrose, calcium sulfate and indanamine are thoroughly mixed and granulated with hot 10% gelatin solution. The wetted mass is passed through a No. 6 mesh screen directly onto drying trays. The granules are dried at 120° C. and passed through a No. 20 mesh screen, mixed with starch, talc and stearic acid and compressed into tablets.

Two tablets are administered three times a day.

What is claimed is:

1. A compound of the formula:

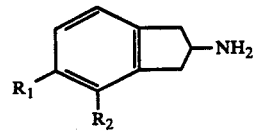

in which:
$R_1$ and $R_2$ are chloro, bromo, fluoro, iodo or trifluoromethyl, $R_1$ and $R_2$ being the same or different or a pharmaceutically acceptable acid addition salt thereof.

2. A compound of claim 1 in which $R_1$ and $R_2$ are chloro.

3. A pharmaceutical composition in dosage unit form for inhibiting phenylethanolamine N-methyltransferase comprising a pharmaceutical carrier and a chemical compound as defined in claim 1.

4. A pharmaceutical composition in dosage unit form for inhibiting phenylethanolamine N-methyltransferase comprising a pharmaceutical carrier and a chemical compound as defined in claim 2.

5. A method of inhibiting phenylethanolamine N-methyltransferase which comprises administering to an animal requiring said treatment an amount sufficient to produce said inhibition a chemical compound as defined in claim 1.

6. A method of inhibiting phenylethanolamine N-methyltransferase which comprises administering to animals requiring said inhibition a dosage unit of from about 50 mg. to about 1000 mg. of a chemical compound as defined in claim 1.

* * * * *